United States Patent [19]
Jonsson et al.

[11] Patent Number: 5,536,469
[45] Date of Patent: Jul. 16, 1996

[54] SYSTEM EMPLOYING A STERILE MEDICAL SOLUTION CONTAINING GLUCOSE OR GLUCOSE-LIKE COMPOUNDS AND A SOLUTION INTENDED FOR SAID SYSTEM

[75] Inventors: Sven Jonsson, Staffanstorp; Per Kjellstrand; Evi Martinson, both of Sodra Sandby; Anders Wieslander, Lund; Eva Svensson; Anders Andren, both of Malmo, all of Sweden

[73] Assignee: Gambro AB, Sweden

[21] Appl. No.: 240,658

[22] PCT Filed: Sep. 14, 1992

[86] PCT No.: PCT/SE92/00631
§ 371 Date: May 16, 1994
§ 102(e) Date: May 16, 1994

[87] PCT Pub. No.: WO93/09820
PCT Pub. Date: May 27, 1993

[30] Foreign Application Priority Data

Nov. 18, 1991 [SE] Sweden .................................. 9103395

[51] Int. Cl.⁶ .............................. A61L 2/00; B01J 19/00
[52] U.S. Cl. ............................. 422/1; 206/568; 206/570; 206/828; 422/25; 422/40; 422/41; 422/256; 604/408; 604/410
[58] Field of Search ................................. 422/1, 25, 40, 422/41, 256; 604/408–410; 206/568, 570, 484, 524.1, 526, 828; 424/681, 678; 514/866, 546, 547, 28

[56] References Cited

U.S. PATENT DOCUMENTS

| | | | |
|---|---|---|---|
| 3,874,384 | 4/1975 | Deindoerfer et al. | 604/408 |
| 4,368,729 | 1/1983 | Dossin | 128/214 D |
| 4,369,779 | 1/1983 | Spencer | 604/408 X |
| 4,657,540 | 4/1987 | Iwamoto et al. | 604/408 |
| 4,994,057 | 2/1991 | Carmen et al. | 604/408 X |
| 4,997,083 | 3/1991 | Loretti et al. | 604/410 X |
| 5,114,004 | 5/1992 | Isono et al. | 604/410 X |
| 5,344,392 | 9/1994 | Senninger et al. | 604/4 |

FOREIGN PATENT DOCUMENTS

| | | |
|---|---|---|
| 0399549 | 5/1990 | European Pat. Off. |
| 9205814 | 9/1991 | WIPO |

OTHER PUBLICATIONS

"In Vitro Testing of Potentially Biocompatible Continuous Ambulatory Peritoneal Dialysis Fluid" Topley et al., Nephrol Dial. Transplant (1991) 6:574–581.

"Toxicity of Peritoneal Dialysis Fluids on Cultured Fibroblasts L-929", Anders Wieslander et al., Kidney International, vol. 40 (1991) pp. 77–79.

Feriani et al., "Will Bicarbonate—CAPD Strengthen the Natural Defence by Having a Physiological pH and a Natural Buffer?" Contr. Nephrol., vol. 57, pp. 101–109 (Karger, Basel 1987).

*Primary Examiner*—Robert Warden
*Assistant Examiner*—Krisanne M. Thornton
*Attorney, Agent, or Firm*—Lerner, David, Littenberg, Krumholz & Mentlik

[57] ABSTRACT

System employing a sterile medical solution containing glucose or glucose polymers, for example nutritional solutions or solutions for peritoneal dialysis, whereby the majority of the solution is packed in a first package, while the glucose or the glucose polymers are separately packed in a second package, whereafter the two packages are heat sterilized. The content of the glucose or glucose polymers in the second package is maintained above 10% by weight, preferably above 20% by weight and most preferably in the order of 40% by weight in order to reduce or totally eliminate the breakdown of glucose. The medical solution after sterilization, mixing and diluting to 1.5% glucose content has an absorbency caused by breakdown products from glucose at 228 nm less than 0.35 and preferably in the order of 0.20 or lower. The medical solution is also defined in that after sterilization, mixing and dilution to 1.5% glucose content it has an ICG-value caused by breakdown products from glucose less than 50% and preferably less than 30%.

78 Claims, 3 Drawing Sheets

5,536,469

SYSTEM EMPLOYING A STERILE MEDICAL SOLUTION CONTAINING GLUCOSE OR GLUCOSE-LIKE COMPOUNDS AND A SOLUTION INTENDED FOR SAID SYSTEM

TECHNICAL FIELD

The present invention relates to a system employing a sterile medical solution comprising glucose or glucose-like compounds, for example nutritional solutions or solutions for peritoneal dialysis, whereby the majority of the solution is packed in a package whilst the glucose or the glucose-like compounds are packed separately in a second package, whereafter the two packages are heat sterilized. By the expression glucose-like compounds is meant for example glucose polymers.

BACKGROUND OF THE INVENTION

It is known to pack a CAPD-solution in a two chamber package from, for example, the article "In Vitro Testing of a Potentially Biocompatible Continuous Ambulatory Peritoneal Dialysis Fluid" by N Topey et al, in Nephrol Dial Transplant (1991) 6:574–581.

The same, or at least a similar, two chamber package having essentially the same inventors is described in international patent application no. WO 91/08008. From e.g. Example 1 of this document it is apparent that the two parts of the package are intended to contain essentially the same quantity of solution. Thus, when the article refers to a larger and smaller package respectively, this is assumed to mean that even in this case the two packages will contain the same quantity of solution, though with the one package being made larger so as to be able to serve as a mixing chamber.

It is known from, for example, the article "Toxity of peritoneal dialysis fluids on cultured fibroblasts L-929" by Anders Wieslander et al, in Kidney International, Vol 40 (1991) pp 77–79, that heat sterilized CAPD-solutions can contain harmful components which can depend on the decomposition of certain compounds, for example glucose, during the sterilization, It is known from, for example, U.S. Pat. Nos. 4,369,779; and 4,753,697 to achieve a sterile coupling between two tubes in various ways, which can be joined to two separate packages.

DESCRIPTION OF THE INVENTION

The present invention can be said to be a development of the above mentioned teachings and relates to a system making use of a sterile medical solution comprising glucose or glucose-like compounds, for example nutritional solutions or solutions for peritoneal dialysis, whereby the majority of the solution is packed in a package whilst the glucose or the glucose-like compounds are separately packed in a second package, whereafter the two packages are heat sterilized.

The system according to the invention is characterized in that the content of the glucose or glucose-like compounds in the second package is maintained above 10% by weight, suitably above 20% by weight, and preferably in the order of 40% by weight. In this manner the breakdown of the packaged product is reduced. At the same time the risk of breakdown is reduced since the product which is sensitive to breakdown need not be in contact with all the compounds in the final solution during heat sterilization.

A further advantage with the invention is the possibility to achieve a final neutral solution with a pH between 6.5 and 7.5. Preferably, a pH of 7.0 is hereby achieved. Here it should be stressed that as far as we are aware no such neutral solutions for PD-dialysis are presently commercially available on the market.

In practice, it has been shown to be possible to make use of a sterilizing temperature between 110° C. and 150° C. and sterilizing times between 180 minutes and 10 minutes from the commencement of heating to cooling to room temperature. At the same time the time interval for the maximum heating should hereby be kept as short as possible, though sufficiently long, of course, to meet the requirements imposed by the authorities so that sufficient death rate of bacteria and spores is obtained.

One possibility is that the two packages are manufactured separately and each one provided with a connection piece or connection tube. Preferably, both packages are completely sealed and each one provided with a connection piece or connection tube made from a heat sealable material and sealed at its extremity with a welded seal, which is intended to be removed or opened under maintained sterility for connection of the two packages together and mixing of their contents. Equipment and procedure for such a connection is described in the above mentioned American patents which are therefore included in the present description. The invention does however also include other known or future sterile connections, for example such as those which are nowadays used for CAPD. An advantage with this embodiment is that the smaller package can be separately heat sterilized at a high temperature for a short period with a short heating period and a short cooling period.

Alternatively, the second package containing said glucose or glucose-like compounds can form a minor part of a double package, for example a double bag, the other part of which forms the first package. The two parts can then be made to communicate with each other for mixing of the contents. The first package should thereby have such volume that in addition to its original contents, it can also accommodate the contents of the second package. An advantage with this embodiment is that an openable connection conduit can be arranged between the two packages already during their manufacture. The heating up time for the smaller package will however be somewhat dependent on the heating up time of the larger package. Even in this case, however, it is desirable that the sterilisation temperature is kept high and the heating up time short.

Suitably, the contents of the smaller glucose-containing package are maintained at a low pH during sterilisation, preferably in the order of 3.5. At the same time, the contents of the two packages during sterilisation should be maintained with such respective pH-values that the final resultant product after mixing is substantially neutral, i.e. with a pH between, for example, 6.5 and 7.5, preferably about 7.0.

The invention further relates to a solution intended for a system of the above defined type. This solution is characterized in that, after sterilization, mixing and diluting to 1.5% glucose content, it has an absorbency caused by breakdown products from glucose at 228 nm of less than 0.35 and preferably 0.20 or lower.

Where the solution according to the invention is intended for peritoneal dialysis the system according to the invention can comprise a smaller package containing 20–500 ml, preferably approximately 65–75 ml glucose with a pH of approximately 3–6, preferably approximately 3.5 and a glucose content of 10–70%, preferably approximately 40%, as well as a larger package containing the remaining compounds, for example Na-lactate 9 g, NaCl 10.8 g, $CaCl_2$ 380 mg and $MgCl_2$ 102 mg, with a pH adjusted to a desired value between 6 and 8.5, and preferably distilled water in a quantity in the order of 2 liters, for example 1935–1925 ml.

The solution according to the invention can also be defined in such a manner that, after sterilization, mixing and diluting to 1.5% glucose content, it has an ICG-value (Inhibition of Cell Growth tested on cultured fibroblasts L-929) caused by breakdown products from glucose of less than 50%, preferably less than 30%. The reason for this definition is, as can be seen from FIG. 4, that the degree of inhibited cell growth bears a close relation to the UV-absorbency at 228 nm. It must however be taken into consideration that the solution should not contain compounds other than glucose or glucose-like compounds with absorbency at 228 am. Should the solution contain other such compounds, then the absorbency will be affected. With knowledge of the included compounds it can however be calculated how much of the absorbency is dependent on breakdown products from glucose.

BEST MODE OF CARRYING OUT THE INVENTION

From the above mentioned article by Anders Wieslander et al it is apparent that existing commercial glucose solutions inhibit the growth of cultured fibroblasts. This implies that the glucose solutions contain one or more substances which are toxic in the biological system.

From a comparison of, for example, sterile filtered solutions and heat sterilized solutions with essentially the same contents, it appears that the toxic effect depends on the substances formed in connection with the heat sterilization or the subsequence storage. Here it should be noted that the authorities in many countries require a sterilization after packaging of the product. In principle this is not possible with sterile filtered solutions.

Figure 4:
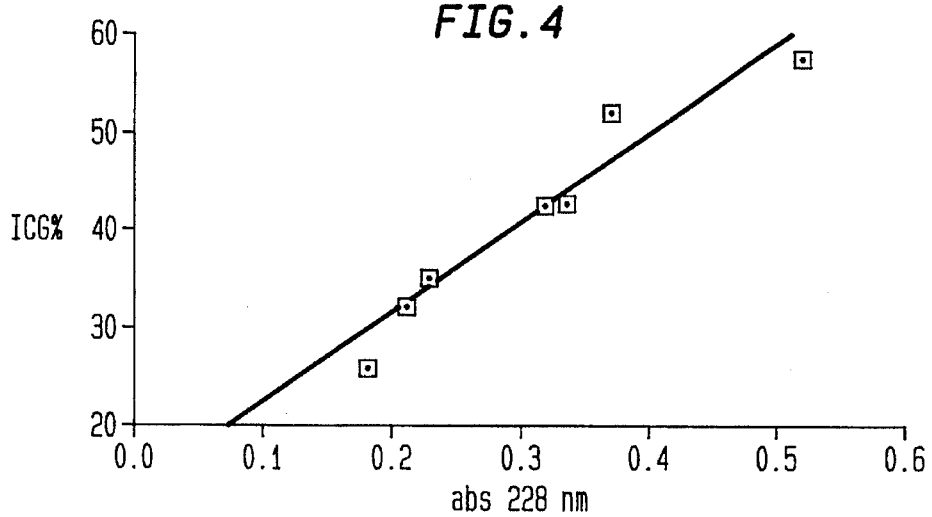
FIG. 4 shows the relationship between the ICG-value and the UV-absorbency at 228 nm after heat sterilizing solutions having different glucose content in pure water.

From, for example, the graph in FIG. 4 it can be seen that the toxic effect (percentage inhibited growth), and thereby also the quantity of toxic substances, is related to the absorbency at 228 nm. This implies that a glucose solution with low absorbency is, from a toxicological view, probably better than a solution with high absorbency at 228 nm.

The aim has been to provide a glucose solution with a considerably lower toxic effect on the biological system compared with sterile glucose solutions commercially available until now. By low toxicity is meant that, accordingly to the invention, a glucose solution diluted to a glucose content of 1.5% may not inhibit cell growth of cultured fibroblasts L-929 through breakdown products (tested according to the above mentioned article by Anders Wisslander et al by more than 50% and preferably by not more than 30%.

Figure 1:
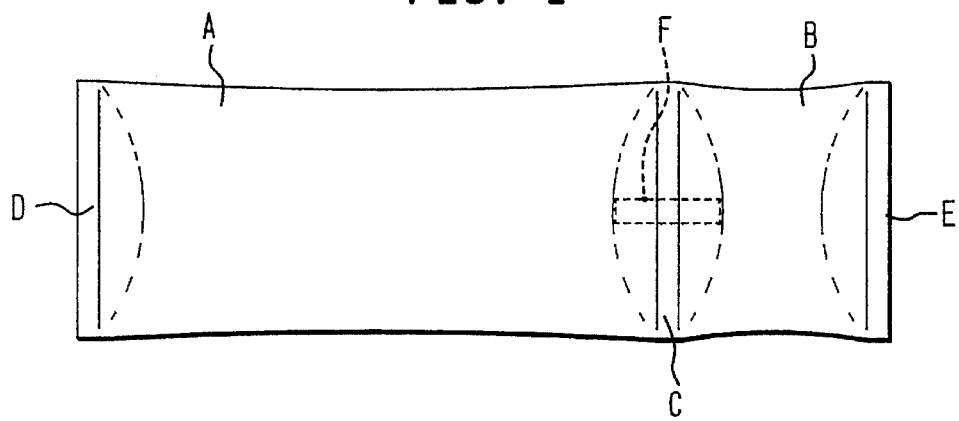
FIG. 1 shows a double package intended to be used in connection with the system according to the invention.
Figure 2:
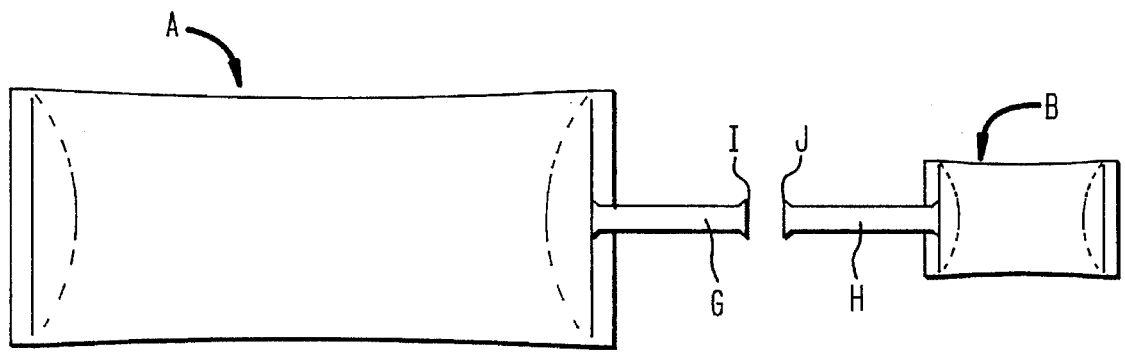
FIG. 2 shows an alternative in the form of two separate bags.
Figure 3:
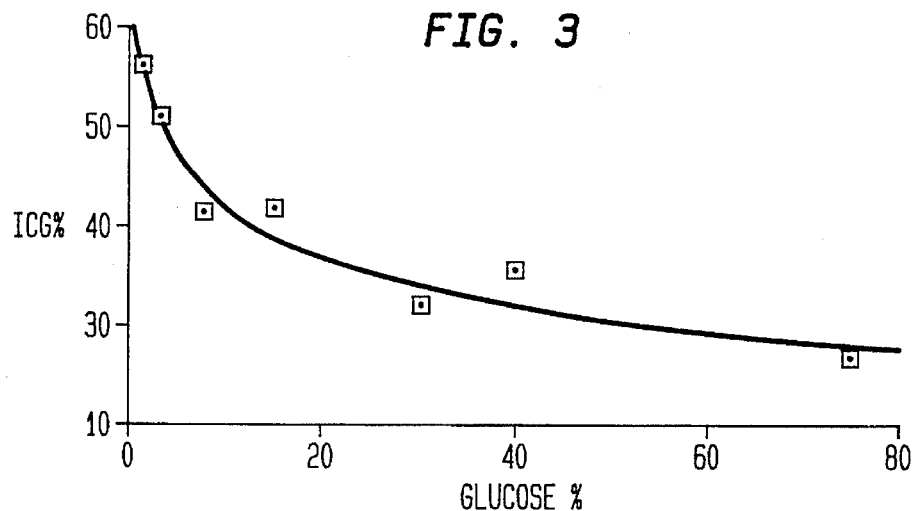
FIG. 3 illustrates the relationship between the glucose content and the ICG-value after heat sterilising of glucose dissolved in pure water.

Two alternative bag systems are shown in FIGS. 1 and 2 which can form the above mentioned packages. In FIG. 1 a double bag is shown consisting of a larger part A and a smaller part B which are separated by a weld or other seal C. The ends of the double package are sealed in a similar manner by welds or other means D, E respectively. The weld C can be entirely broken open. Alternatively, the two bag parts A and B can be connected already during manufacture by means of a tube F containing a suitable breakable seal, for example a conventional breakpin.

The alternative shown in FIG. 2 consists of a separate larger bag A and a similarly separate smaller bag B. The two bags are provided with connection pieces or connection conduits denoted by G and H respectively. Each of these connection pieces can be provided with sterile connecting halves for sterile connection. In the shown example it is intended that they be terminated with an end sealing weld I, J respectively. A sterile connection can thus be achieved in the manner described by way of example in said above mentioned U.S. Pat. Nos. 4,369,779 and 4,753,697, the subject matter of which is incorporated herein by reference. The contents of these are therefore included in the present description.

The alternative according to FIG. 2 enjoys the advantage that the bag A can be heat sterilized in a conventional manner at the same time that a particularly quick heating and cooling of the bag B can be achieved if it is manufactured from two plastic sheets laid one on top of the other which are joined to each other along the periphery and which have dimensions such that the layer of glucose solution can be maintained relatively thin during the heat sterilization. By way of example, a bag containing 75 ml of glucose solution can have the dimensions 10 cm by 10 cm.

The larger bag A can, if used in peritoneal dialysis, contain a salt solution with the contents Na-lactate 9 g, NaCl 10.8 g, $CaCl_2$ 380 mg and $MgCl_2$ 102 mg (the composition can be varied somewhat). The pH should be adjusted to the desired value between 7 and 9. Finally, the bag preferably contains distilled water in a quantity in the order of 2 liters, for example 1925–1935 ml. The heat sterilization is envisaged to take place in a conventional manner in an autoclave with suitably adapted time and temperatures.

The small bag B can contain glucose concentrate, for example 20–500 ml, preferably 65–75 ml, 10–70% glucose, preferably 40%. The pH-value should lie between 3 and 6, preferably about 3.5. The sterilization may be effected in a autoclave at a temperature between 110° C. and 145° C., suitably above 120° C. and preferably at 130° C. With the embodiment according to FIG. 1 the bag part B is of course sterilized at the same time as the bag part A. With the embodiment according to FIG. 2, the bag B is however suitably sterilized separately so that the necessary sterilizing temperature can be quickly reached and thereafter obtain a quick cooling.

During the trials $F_0$ equal to 40 was sought, though in practice this value varied somewhat. By $F_0$ is meant the time in minutes which the solution should need to be maintained at 121° C. in order to become sterile in accordance with that which is demanded by supervising authorities. $F_0$ equal to 10 implies therefore that the product must be maintained at 121° C. for 10 minutes in order to achieve sterility.

The following table presents the results of a number of experimental tests. In line 1 a sterile-filtered, i.e. non-heat sterilized, complete solution for PD containing 1.5% glucose was tested. The three following lines show the results with heat sterilization with differing $F_0$ of a complete PD-solution in which the glucose was added at the beginning. These solutions also included 1.5% glucose.

The last three lines give the results of tests on complete mixing with which a glucose solution was heat sterilized separately so that first after sterilizing it could be mixed with remaining compounds included in the PD-solution. The glucose concentration was hereby maintained during the sterilizing at about 40%. After the mixing together, this was reduced to 1.5% in agreement with the concentration of remaining solutions in the comparative tests.

From the table it can further be seen that with help of the invention the concentration of acetaldehyde can be kept low by separately sterilising the glucose solution. Acetaldehyde is a typical breakdown product from glucose and the amount of this product should be kept below 1.0 ppm, suitably below 0.1 ppm and preferably in the order of 0.01–0.001 ppm.

In FIG. 4 the relationship is shown between the absorbency at 228 nm and the ICG-values after heat sterilising of a number of glucose solutions in pure water. The graph shows that the condition for an acceptable product can either be defined by means of a low absorbency value or low ICG-value.

Figure 5:
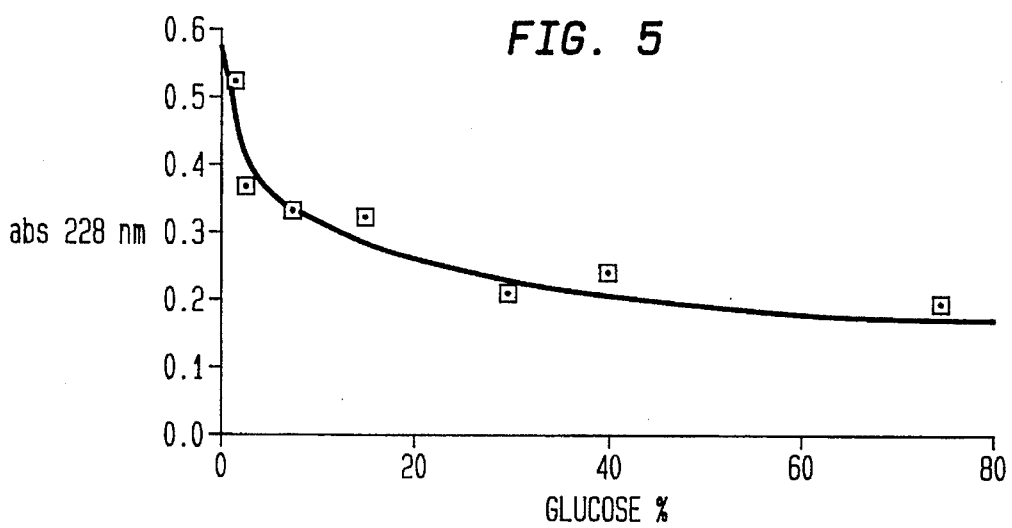
FIG. 5 show the absorbency at 228 nm after heat sterilizing solutions with different glucose contents in pure water.

FIG. 5 shows the absorbency at 228 nm after heat-sterilising for a number of glucose solutions in pure water. The higher the glucose concentration is maintained, the lower the absorbency and thus also the ICG-value becomes. In practice, however, the glucose concentration should not be maintained above about 40%. In addition, particularly at low temperatures there is a risk of crystal-formation.

Figure 6:
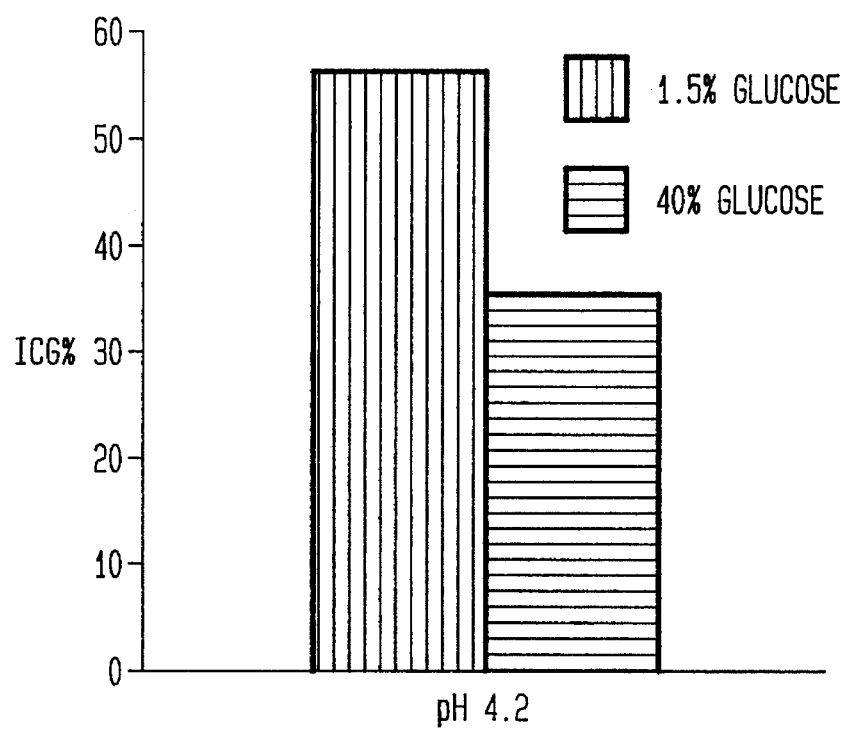
FIG. 6 shows in the form of a bar chart a comparison between the ICG-values after heat sterilizing water solutions with 1.5% and 40% glucose respectively.
Figure 7:
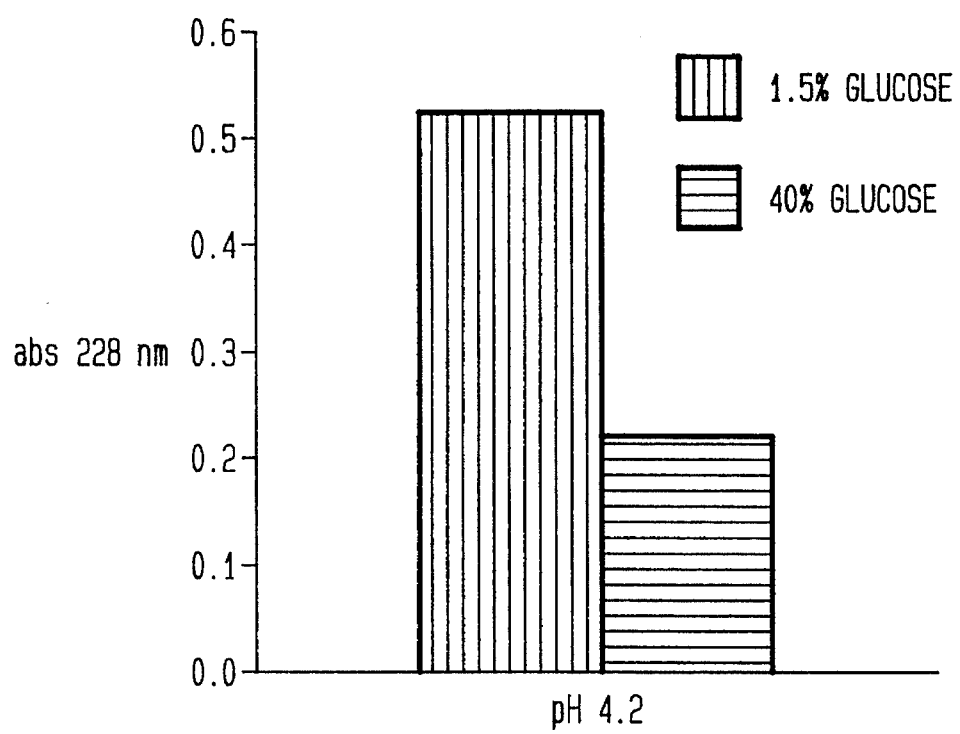
FIG. 7 illustrates in the same manner a comparison between the absorbency at 228 nm after heat sterilizing water solutions with 1.5% and 40% glucose respectively.

Finally, FIGS. 6 and 7 show respectively a comparison between the absorbency values at 228 nm for a sterilized water solution with 1.5% glucose in complete condition and a corresponding 1.5% solution in which the glucose was sterilized separately at a concentration of 40%.

The invention has been described in the above particularly in connection with peritoneal dialysis, more particularly CAPD. It will however be apparent that the invention can also be suitable in connection with other sterile solutions containing glucose or glucose-like compounds, for example polymers of glucose. By way of example the invention can be suitable in connection with sterilization of nutritional solutions containing glucose or glucose-like compounds which otherwise will be problematic in terms of breakdown products in connection with heat sterilization.

Table

The toxicity and breakdown products in PD-solutions after heat sterilizing. The PD-solutions were sterilized either as a conventional bag or double bag with glucose concentrate. All values refer to finally mixed end products.

| Test solution | $F_0$ | Absorbency 228 nm | 284 nm | Acetaldehyde ppm | Formaldehyde ppm | Cytotoxicity % |
|---|---|---|---|---|---|---|
| Sterile-filtered | 0 | 0.295 | 0.011 | 0.005 | <0.005 | 16 |
| Complete | 10 | 0.467 | 0.053 | 4.0 | 0.005 | 44 |
| Complete | 20 | 0.666 | 0.110 | 8.8 | 0.005 | 73 |
| Complete | 30 | 0.765 | 0.150 | 11.6 | 0.2 | 83 |
| Glucose conc | 10 | 0.404 | 0.074 | 0.005 | <0.005 | 21 |
| Glucose conc | 20 | 0.419 | 0.112 | 0.005 | <0.005 | 25 |
| Glucose conc | 30 | 0.414 | 0.158 | 0.005 | <0.005 | 27 |

We claim:

1. A system for providing a sterile medical solution comprising a first heat-sterilizable package containing a first portion of a medical solution, a second heat-sterilizable package containing a second portion of said medical solution comprising glucose or a glucose polymer at a concentration of greater than about 20% by weight, said first portion of said medical solution being larger than said second portion of said medical solution, and sterile connecting means for interconnecting said first and second packages whereby following sterilization of said first and second packages said first and second packages can be interconnected through said sterile connecting means and said first and second portions of said medical solutions can be combined while the formation of toxic substances during said sterilization is substantially prevented therein.

2. The system of claim 1 wherein said sterile medical solution comprises a nutritional solution or solutions for peritoneal dialysis.

3. The system of claim 1 wherein said second portion of said medical solution in said second package comprises a glucose-containing composition at a concentration of about 40% by weight.

4. The system of claim 1 wherein said first and second packages comprise separate portions of a single package comprising a double bag.

5. The system of claim 1 wherein said first package comprises a volume sufficient to accommodate both said first and second portions of said medical solution.

6. The system of claim 1 wherein said first portion of said medical solution comprises sodium lactate, sodium chloride, calcium chloride, magnesium chloride, and water and said second portion of said medical solution comprises glucose.

7. The system of claim 6 wherein said first portion of said medical solution includes about 9 grams of said sodium lactate, about 0.8 grams of said sodium chloride, about 380 milligrams of said calcium chloride, about 102 milligrams of said magnesium chloride, and about 2 liters of said water, and said second portion of said medical solution comprises between about 20 and 500 milliliters of said glucose.

8. The system of claim 7 wherein said second portion of said medical solution comprises between about 65 and 75 milliliters of said glucose.

9. The system of claim 1 wherein said first portion of said medical solution has a higher pH than said second portion of said medical solution.

10. The system of claim 9 wherein said first portion of said medical solution has a pH of between about 6 and 8.5 and said second portion of said medical solution has a pH of between about 3 and 6.

11. The system of claim 10 wherein said second portion of said medical solution has a pH of about 3.5.

12. The system of claim 11 wherein said first portion of said medical solution has a first pH and said second portion of said medical solution has a second pH, said first and second pH's being such that after mixing said medical solution has a substantially neutral pH.

13. The system of claim 12 wherein after mixing said medical solution has a pH of between about 6.5 and 7.5.

14. The system of claim 13 wherein after mixing said medical solution has a pH of about 7.0.

15. The system of claim 1 wherein said first and second packages are disposed with respect to each other in a manner such that said second package can be separately sterilized from said first package at a higher temperature and for a shorter time than said first package.

16. The system of claim 1 wherein said first and second packages are completely sealed, and said sterile connecting means comprises a first sterile connecting member connected to said first package and a second sterile connecting member connected to said second package, each of said first and second sterile connecting members including a breakable seal whereby said first and second portions of said medical solution can be mixed therefrom.

17. The system of claim 16 where each of said first and second sterile connecting members comprises heat sealable material, and said breakable seal comprises sealing welds on said first and second sterile connecting members.

18. A method for providing a sterile medical solution comprising providing a first portion of a medical solution in a first heat-sterilizable package, providing a second portion of said medical solution in a second heat-sterilizable package, said second portion of said medical solution comprising glucose or a glucose polymer at a concentration of greater than about 20% by weight, said first portion of said medical solution being larger than aid second portion of said medical solution, heat sterilizing said first and second packages, and interconnecting said first and second packages following said heat sterilizing whereby said first and second portions of said medical solutions are combined while the formation of toxic substances during said sterilization is substantially prevented therein.

19. The method of claim 18 wherein said heat sterilizing of said second package is carried out at a temperature of between about 110° and 150° C.

20. The method of claim 19 wherein said heat sterilizing of said second package is carried out at a temperature of greater than about 120° C.

21. The method of claim 19 wherein said heat sterilizing of said second package begins with initiating the heating of said second package to said temperature and concludes with the cooling of said heated second package to room temperature.

22. The method of claim 21 wherein said heat sterilizing of said second package takes place during a time interval of between about 10 and 180 minutes.

23. The method of claim 18 including diluting said combined first and second portions of said medical solution to a glucose content of approximately 1.5% by weight, said diluted first and second portions of said medical solution having an absorbency caused by breakdown products from said glucose at 228 nm of less than about 0.35.

24. The method of claim 23 wherein said diluted first and second portions of said medical solutions has an absorbency caused by breakdown products from said glucose at 228 nm of about 0.2 or less.

25. The method of claim 18 including diluting said combined first and second portions of said medical solution to a glucose content of approximately 1.5% by weight, said diluted first and second portions of said medical solution having an ICG-value caused by breakdown products from said glucose of less than about 50%.

26. The method of claim 25 wherein said diluted first and second portions of said medical solution have an ICG-value caused by breakdown products from said glucose of less than about 30%.

27. The method of claim 18 including diluting said combined first and second portions of said medical solution, said diluted first and second portions of said medical solution including acetaldehyde as a breakdown product from said glucose in an amount of less than about 1.0 ppm.

28. The method of claim 27 wherein said combined first and second portions of said medical solution have an acetaldehyde content of less than about 0.1 ppm.

29. The method of claim 28 wherein said combined first and second portions of said medical solution have an acetaldehyde content of between about 0.01 and 0.001 ppm.

30. The method of claim 18 wherein said second portion of said medical solution comprises a glucose-containing composition at a concentration of about 40% by weight.

31. The method of claim 18 wherein said first portion of said medical solution comprises sodium lactate, sodium chloride, calcium chloride, magnesium chloride, and water and said second portion of said medical solution comprises glucose.

32. The method of claim 31 wherein said first portion of said medical solution comprises about 9 grams of said sodium lactate, about 10.8 grams of said sodium chloride, about 380 milligrams of said calcium chloride, about 102 milligrams of said magnesium chloride, and about 2 liters of said water and said second portion of said medical solution comprises between about 20 and 500 milliliters of said glucose.

33. The method of claim 32 wherein said second portion of said medical solution comprises between about 65 and 75 milliliters of said glucose.

34. The method of claim 18 wherein said first portion of said medical solution has a higher pH than said second portion of said medical solution.

35. The method of claim 34 wherein said first portion of said medical solution has a pH of between about 6 and 8.5 and said second portion of said medical solution has a pH of between about 3 and 6.

36. The method of claim 35 wherein said second portion of said medical solution has a pH of about 3.5.

37. The method of claim 18 wherein said first portion of said medical solution has a first pH and said second portion of said medical solution has a second pH, wherein after mixing of said first and second medical solutions said medical solution has a substantially neutral pH.

38. The method of claim 37 wherein said medical solution has a pH of between about 6.5 and 7.5.

39. The method of claim 38 wherein said medical solution has a pH of about 7.0.

40. The method of claim 18 wherein said sterile medical solution comprise a nutritional solution or solutions for peritoneal dialysis.

41. A method for providing a sterile medical solution suitable for peritoneal dialysis comprising the steps of providing a bag system having first and second separate compartments; providing in said second compartment a second portion of said solution comprising glucose dissolved in water at a concentration of greater than about 20% and at a pH-value in the range of about 3 to 6; providing in said first compartment a first portion of said solution comprising the remaining components for said solution including at least one component selected from the group consisting of sodium lactate, sodium chloride, potassium chloride, calcium chloride and magnesium chloride; said first portion of said medical solution being larger than said second portion of said medical solution; heat sterilizing said bag system at a temperature of greater than about 110° C. while the glucose is prevented from forming toxic substances; and combining the contents of said first and the second compartments in one of said compartments to form said sterile medical solution.

42. The method of claim 41 including diluting said combined first and second portions of said medical solution to a glucose content of approximately 1.5% by weight, said diluted first and second portions of said medical solution having an absorbency caused by breakdown products from said glucose at 228 nm of less than about 0.35.

43. The method of claim 41 including diluting said combined first and second portions of said medical solution to a glucose content of approximately 1.5% by weight, said diluted first and second portions of said medical solution having an ICG-value caused by breakdown products from said glucose of less than about 50%.

44. The method of claim 41 including diluting said combined first and second portions of said medical solution, said diluted first and second portions of said medical solution including acetaldehyde as a breakdown product from said glucose in an amount of less than about 1.0 ppm.

45. The method of claim 41 wherein said second portion of said medical solution comprises a glucose-containing composition at a concentration of about 40% by weight.

46. The method of claim 41 wherein said first portion of said medical solution comprises sodium lactate, sodium chloride, calcium chloride, magnesium chloride, and water and said second portion of said medical solution comprises glucose.

47. The method of claim 46 wherein said first portion of said medical solution comprises about 9 grams of said sodium lactate, about 10.8 grams of said sodium chloride, about 380 milligrams of said calcium chloride, about 102 milligrams of said magnesium chloride, and about 2 liters of said water and said second portion of said medical solution comprises between about 20 and 500 milliliters of said glucose.

48. The method of claim 41 wherein said first portion of said medical solution has a pH of between about 6 and 8.5 and said second portion of said medical solution has a pH of between about 3 and 6.

49. The method of claim 41 wherein said first portion of said medical solution has a first pH and said second portion of said medical solution has a second pH, wherein after mixing of said first and second medical solutions said medical solution has a substantially neutral pH.

50. A method for providing a sterile medical solution suitable for nutritional administration comprising the steps of providing a bag system having first and second separate compartments; providing in said second compartment a second portion of said solution comprising glucose dissolved in water at a concentration of greater than about 20% and at a pH-value in the range of about 3 to 6; providing in said first compartment a first portion of said solution comprising the remaining components for said solution including at least one component selected from the group consisting of sodium lactate, sodium chloride, potassium chloride, calcium chloride and magnesium chloride; said first portion of said medical solution being larger than said second portion of said medical solution; heat sterilizing said bag system at a temperature of greater than about 110° C. while the glucose is prevented from forming toxic substances; and combining the contents of said first and the second compartments in one of said compartments to form said sterile medical solution.

51. The method of claim 50 including diluting said combined first and second portions of said medical solution to a glucose content of approximately 1.5% by weight, said diluted first and second portions of said medical solution having an absorbency caused by breakdown products from said glucose at 228 nm of less than about 0.35.

52. The method of claim 50 including diluting said combined first and second portions of said medical solution to a glucose content of approximately 1.5% by weight, said diluted first and second portions of said medical solution having an ICG-value caused by breakdown products from said glucose of less than about 50%.

53. The method of claim 50 including diluting said combined first and second portions of said medical solution, said diluted first and second portions of said medical solution including acetaldehyde as a breakdown product from said glucose in an amount of less than about 1.0 ppm.

54. The method of claim 50 wherein said second portion of said medical solution comprises a glucose-containing composition at a concentration of about 40% by weight.

55. The method of claim 50 wherein said first portion of said medical solution comprises sodium lactate, sodium chloride, calcium chloride, magnesium chloride, and water and said second portion of said medical solution comprises glucose.

56. The method of claim 55 wherein said first portion of said medical solution comprises about 9 grams of said sodium lactate, about 10.8 grams of said sodium chloride, about 380 milligrams of said calcium chloride, about 102 milligrams of said magnesium chloride, and about 2 liters of said water and said second portion of said medical solution comprises between about 20 and 500 milliliters of said glucose.

57. The method of claim 50 wherein said first portion of said medical solution has a pH of between about 6 and 8.5 and said second portion of said medical solution has a pH of between about 3 and 6.

58. The method of claim 50 wherein said first portion of said medical solution has a first pH and said second portion of said medical solution has a second pH, wherein after mixing of said first and second medical solutions said medical solution has a substantially neutral pH.

59. A system for providing a sterile medical solution suitable for peritoneal dialysis comprising a bag system having first and second separate compartments; said second compartment containing a second portion of said solution comprising glucose dissolved in water at a concentration of greater than about 20% and at a pH-value in the range of about 3 to 6; said first compartment containing a first portion of said solution comprising the remaining components for said solution including at least one component selected from the group consisting of sodium lactate, sodium chloride, potassium chloride, calcium chloride and magnesium chloride; said first portion of said medical solution being larger than said second portion of said medical solution; said bag system being heat sterilized at a temperature of greater than about 110° C. while the glucose is prevented from forming toxic substances; and combining means for combining the contents of said first and second compartments in one of said compartments to form said sterile medical solution.

60. The system of claim 59 wherein said second portion of said medical solution in said second compartment comprises a glucose-containing composition at a concentration of about 40% by weight.

61. The system of claim 59 wherein said first and second compartments comprise separate portions of a single package comprising a double bag.

62. The system of claim 59 wherein said first compartment comprises a volume sufficient to accommodate both said first and second portions of said medical solution.

63. The system of claim 59 wherein said first portion of said medical solution comprises sodium lactate, sodium chloride, calcium chloride, magnesium chloride, and water and said second portion of said medical solution comprises glucose.

64. The system of claim 63 wherein said first portion of said medical solution includes about 9 grams of said sodium lactate, about 10.8 grams of said sodium chloride, about 380 milligrams of said calcium chloride, about 102 milligrams of said magnesium chloride, and about 2 liters of said water, and said second portion of said medical solution comprises between about 20 and 500 milliliters of said glucose.

65. The system of claim 59 wherein said first portion of said medical solution has a pH of between about 6 and 8.5 and said second portion of said medical solution has a pH of between about 3 and 6.

66. The system of claim 59 wherein said first portion of said medical solution has a first pH and said second portion of said medical solution has a second pH, said first and second pH's being such that after mixing said medical solution has a substantially neutral pH.

67. The system of claim 66 wherein after mixing said medical solution has a pH of between about 6.5 and 7.5.

68. The system of claim 59 wherein said first and second compartments are disposed with respect to each other in a manner such that said second compartment can be separately sterilized from said first compartment at a higher temperature and for a shorter time than said first compartment.

69. A system for providing a sterile medical solution suitable for nutritional administration comprising a bag system having first and second separate compartments; said second compartment containing a second portion of said solution comprising glucose dissolved in water at a concentration of greater than about 20% and at a pH-value in the range of about 3 to 6; said first compartment containing a first portion of said solution comprising the remaining components for said solution including at least one component selected from the group consisting of sodium lactate, sodium chloride, potassium chloride, calcium chloride and magnesium chloride; said first portion of said medical solution being larger than said second portion of said medical solution; said bag system being heat sterilized at a temperature of greater than about 110° C. while the glucose is prevented from forming toxic substances; and combining means for combining the contents of said first and second compartments in one of said compartments to form said sterile medical solution.

70. The system of claim 69 wherein said second portion of said medical solution in said second compartment comprises a glucose-containing composition at a concentration of about 40% by weight.

71. The system of claim 69 wherein said first and second compartments comprise separate portions of a single package comprising a double bag.

72. The system of claim 69 wherein said first compartment comprises a volume sufficient to accommodate both said first and second portions of said medical solution.

73. The system of claim 69 wherein said first portion of said medical solution comprises sodium lactate, sodium chloride, calcium chloride, magnesium chloride, and water and said second portion of said medical solution comprises glucose.

74. The system of claim 73 wherein said first portion of said medical solution includes about 9 grams of said sodium lactate, about 10.8 grams of said sodium chloride, about 380 milligrams of said calcium chloride, about 102 milligrams of said magnesium chloride, and about 2 liters of said water, and said second portion of said medical solution comprises between about 20 and 500 milliliters of said glucose.

75. The system of claim 69 wherein said first portion of said medical solution has a pH of between about 6 and 8.5 and said second portion of said medical solution has a pH of between about 3 and 6.

76. The system of claim 69 wherein said first portion of said medical solution has a first pH and said second portion of said medical solution has a second pH, said first and second pH's being such that after mixing said medical solution has a substantially neutral pH.

77. The system of claim 76 wherein after mixing said medical solution has a pH of between about 6.5 and 7.5.

78. The system of claim 69 wherein said first and second compartments are disposed with respect to each other in a manner such that said second compartment can be separately sterilized from said first compartment at a higher temperature and for a shorter time than said first compartment.

\* \* \* \* \*

UNITED STATES PATENT AND TRADEMARK OFFICE
CERTIFICATE OF CORRECTION

PATENT NO. : 5,536,469
DATED : July 16, 1996
INVENTOR(S) : Jonsson, et al.

It is certified that error appears in the above-indentified patent and that said Letters Patent is hereby corrected as shown below:

Column 3, line 19, "am" should --nm--.
Column 4, line 10, "Wisslander" should read --Wieslander--.
Column 6, line 50, "0.8" should read --10.8--.
Column 6, line 67, "11" should read --1--.

Signed and Sealed this

Third Day of December, 1996

Attest:

BRUCE LEHMAN

*Attesting Officer*  *Commissioner of Patents and Trademarks*